US006376743B1

(12) United States Patent
Yanagimachi

(10) Patent No.: US 6,376,743 B1
(45) Date of Patent: Apr. 23, 2002

(54) MAMMALIAN TRANSGENESIS BY INTRACYTOPLASMIC SPERM INJECTION

(75) Inventor: Ryuzo Yanagimachi, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 09/371,648

(22) Filed: Aug. 10, 1999

Related U.S. Application Data

(60) Provisional application No. 60/133,970, filed on May 13, 1999, and provisional application No. 60/096,078, filed on Aug. 11, 1998.

(51) Int. Cl.$^7$ .................. A01K 67/027; A01K 67/00; A01K 67/033; G01N 33/00; C12N 15/00
(52) U.S. Cl. .................. 800/18; 800/3; 800/13; 800/14; 800/21; 435/325; 435/455
(58) Field of Search .................. 435/287.1, 331, 435/325, 455; 422/102; 536/25.42; 800/18, 3, 13, 21, 14

(56) References Cited

FOREIGN PATENT DOCUMENTS

WO  WO 00/08924  2/2000

OTHER PUBLICATIONS

Mullins et al., 1996, Journal of Clinical Investigations, 98: S37–40.*
Kappel et al., 1992, Current Opinion in Biotechnology, 3: 548–553.*
Wall et al., 1996, Theriogenology, 45: 57–68.*
Strojek et al., 1988 Genetic Engineering: Principles and Methods, v10 pp. 221–246.*
Lavitrano et al., 1989, Cell, 57:717–723. Part of IDS.*
Kuretake et al., 1996, Biol of Reprod., 55: 789–795. Part of IDS.*
Atkinson, P.W. et al. (1991). Association of exogenous DNA with cattle and insect spermatozoa in vitro. *Mol. Reprod. Dev.* 29:1–5.
Chan, A.W.S. et al. (2000). Foreign DNA transmission by ICSI: injection of of spermatozoa bound with exogenous DNA results in embryonic GFP expression and live Rhesus monkey births. *Mol. Hum. Reprod.* 6:26–33.
Fernandez, M.A. et al. (1999). Sperm–mediated gene transfer into oocytes of the golden hamster: assessment of sperm function. *Ind. J. of Exp. Biol.* 37:1085–1092.
Gandolfi, F. (1998). Spermatozoa, DNA binding and transgenic animals. *Transgenic Research* 7:147–155.
Gandolfi, F. (2000). Sperm–mediated transgenesis. *Theriogenology* 53:127–137.
Kuznetsov, A.V. and Kuznetsova, I.V. (1995). Binding of exogenous DNA pRK31acZ by the rabbit spermatozoa, its transfer in the oocytes and expression in the preimplantation embryos. 26:300–309. (Abstract in English, see last page).

Magnano, A.R. et al. (1998). Sperm/DNA interaction: integration of foreign DNA sequences in the mouse sperm genome. *J. Reprod. Immuno.* 41;187–196.
Patil, J.G. and Khoo, H.W. (1996). Nuclear internalization of foreign DNA by zebrafish spermatozoa and its enhancement by electroporation *J. Exp. Zool.* 274:121–129.
Smith, K.R. (1999). Sperm cell mediated transgenesis: a review. *Animal Biotechnology* 10:1–13.
Spadafora, C. (1998). Sperm cells and foreign DNA: a controversial relation. *BioEssays* 20:955–964.
Tsai, H.J. et al. (1997). Sperm as a carrier to introduce an exogenous DNA fragment into the oocyte of Japanese abalone (Haliotis divorsicolor suportextia). *Transgenic Research* 6:85–95.
Inoue, K. & Yamashita, S. The Techniques Using Electroporation to Generate Transgenic Fish. in *Transgenic Animals: Generation and Use*, p. 129–132, France: harwood academic publishers (1977).
Lavitrano, M. et al. Interaction between sperm cells and exogenous DNA: sperm mediated gene transfer. *Cell Biology International* 18: 464 (1994).
Lavitrano, M. et al. Sperm–mediated gene transfer: production of pigs transgenic for a human regulator of complement activation. *Transplantation Proceedings* 29: 3508–3509 (1997).
Nakanishi, A. & Iritani, A. Gene transfer in the chicken by sperm–mediated methods. *Molecular Reproduction and Development* 36: 258–261 (1993).
Niemann, H. A survey of sperm–mediated DNA–transfer in farm animals. Proceedings of the Third International Conference on Boar Semen Preservation: Boar Semen Preservation III 31: 211–216 (1996).
Reventos, J. & Munell, F. Transgenic animal models in reproductive endocrine research. *European Journal of Endocrinology* 136: 566–580 (1997).
Schellander, K. & Berm, G. The Direct Gene Transfer Through Mammalian Spermatozoa in *Transgenic Animals: Generation and Use*, p. 41–44, France: harwood academic publishers (1977).
Xin, S.Y. et al. The production of transgenic sheep by sperm mediated gene tranfer method. *Cell Biology International* 18: 464 (1994).
Gordon, J.W. et al. Genetic transformation of mouse embryos by microinjection of purified DNA. *PNAS U.S.A.* 77, 7380.

(List continued on next page.)

*Primary Examiner*—Deborah J. R. Clark
*Assistant Examiner*—Peter Paras, Jr.
(74) *Attorney, Agent, or Firm*—Jones, Day, Reavis & Pogue

(57) ABSTRACT

Coinjection of unfertilized mouse oocytes with sperm heads and exogenous nucleic acid encoding a transgene results in transgene-expressing embryos, reflecting nucleic acid-sperm head association before coinjection. Nonselective transfer to surrogate mothers of embryos resulting from coinjection produced offspring expressing the integrated transgene.

20 Claims, 3 Drawing Sheets

OTHER PUBLICATIONS

Gordon, J.W. and F.H. Ruddle (1981). Integration and stable germ line transmission of genes injected into mouse pronuclei. *Science* 214, 1244.

Palmiter, R.D. and R.L. Brinster (1986). Germ–line transformation of mice. *Annu. Rev. Genet.* 20, 465.

J.W. Gordon (1989). Transgenic animals. *Int. Rev. Cytol.* 115, 171.

Evans, M.J. and M.H. Kaufman (1981). Establishment in culture of pluripotential cells from mouse embryos. *Nature* 292, 154.

Kuehn, M. et al. (1987). A potential animal model for Lesch–Nyhan syndrome through introduction of HPRT mutations into mice. *Nature* 326, 295.

Jähner, D. et al. (1985). Insertion of the bacterial gpt gene into the germ line of mice by retroviral infection. *PNAS U.S.A.* 82, 6297.

Chan, A.W.S. et al. (1998). Transgenic cattle produced by reverse–transcribed gene tranfer in oocytes. *PNAS U.S.A.* 95, 14028.

Kanegae, Y. et al. (1995). Efficient gene activation in mammalian cells by using recombinant adenovirus expressing site–specific Cre recombinase. *Nucleic Acids Res.* 23 3816.

Lavitrano, M. et al. (1989). Sperm cells as vectors for introducing foreign DNA into eggs: Genetic transformation of mice. *Cell* 57, 717.

Brinster, R.N. et al. (1989). No simple solution for making transgenic mice. *Cell* 59, 239.

Maione, B. et al. (1998). Sperm–mediated gene transfer in mice. *Mol. Reprod. Dev.* 59, 406.

Huget, E. and P. Esponda (1998). Foreign DNA introduced into the vas deferens is gained by mammalian spermatozoa. *Mol. Reprod. Dev.* 51, 42.

Kimura, Y. et al. (1998). Analysis of mouse oocyte activation suggests the involvement of sperm perinuclear material, *Biol. Reprod.* 58, 1407.

Wakayama, T. and R. Yanagimachi (1998). Development of normal mice from oocytes injected with freeze–dried spermatozoa. *Nature Biotechnol.* 16, 639.

Chatot, C.L. et al. (1990). Development of 1–cell embryos from different strains of mice in C28 medium. *Biol. Reprod.* 42, 432.

Niwa, H. et al. (1991). Efficient selection for high–expression transfectants with a novel eukaryotic vector. *Gene* 108, 193.

Zhang, G. et al. (1996). An enhanced green fluorescent protein allows sensitive detection of gene transfer in mammalian cells. *Biochem. Biophys. Res. Commun.* 227, 707.

Takada, T. et al. (1997). Selective production of transgenic mice using green fluorescent protein as a marker. *Nature Biotechnol.* 15, 458.

Wakayama, T. et al. (1998). Production of normal offspring from mouse oocytes injected with spermatozoa cryopreserved with or without cryoprotection. *J. Reprod. Fertil.* 112, 11.

Tsukui, T. et al. (1996). Transgenesis by adenovirus–mediated gene transfer into mouse zona–free eggs. *Nature Biotechnol.* 14, 982.

Lavitrano, M. et al. (1992). The interaction between exogenous DNA and sperm cells. *Mol. Reprod. Dev.* 31, 61.

Bos–Mikich, A. et al. (1997). Meiotic and mitotic $Ca^{2+}$ oscillations affect cell composition in resulting blastocysts. *Dev. Biol.* 182, 172.

Longo, F.J. et al. (1987). Basic proteins of the perinuclear theca of mammalian spermatozoa and spermatids: A novel class of cytoskeletal elements. *J. Cell Biol.* 105, 1105.

Maione, B. et al. (1997). Activation of endgenous nucleases in mature sperm cells upon interaction with exogenous DNA. *DNA and Cell Biol.* 16, 1087.

Ladha, S. et al. (1997). Lateral mobility of plasma membrane lipids in bull spermatoza: heterogeneity between surface domains and rigidification following cell death. *J. Cell Sci.* 110, 1041.

Tsien, R.Y. (1998). The green fluorescent protein, *Annu. Rev. Biochem.* 67, 509.

Kroll, K.L. and E. Amaya (1996). Transgenic Xenopus embryos from sperm nuclear transplantations reveal FGF signaling requirements during gastrulation. *Development* 122, 3173.

R. Yanagimachi (1994) in *The Physiology of Reproduction*, E. Knobil and J. D. Neill, Eds. Raven Press, ed. 2, pp. 189–317.

Goto, K. et al. (1990). Fertilisation of bovine oocytes by the injection of immobilised, killed spermatozoa, *Vet. Rec.* 127, 517.

Kim, N.–H et al. (1998). Fertilization of porcine oocytes following intracytoplasmic spermatozoon or isolated sperm–head injection. *Mol. Reprod. Dev.* 51, 436.

Kimura, Y. and R. Yanagimachi (1995). Intracytoplasmic sperm injection in the mouse. Biol. Reprod. 52, 709.

Kuretake, S. et al. (1996). Fertilization and development of mouse oocytes injected with isolated sperm heads. *Biol. Reprod.* 55, 789.

Sutovsky, P. et al. (1997). The removal of the sperm perinuclear theca and its association with the bovine oocyte surface during fertilization. *Developmental Biol.* 188, 75.

Yanagimachi, R. and Y.D. Noda (1970). Electron microscope studies of sperm incorporation into the golden hamster egg. *Am. J. Anat.* 128, 429.

Cibelli, J.B. et al. (1998). Transgenic bovine chimeric offspring produced from somatic ell–derived stem–like cells. *Nature Biotechnol.* 16, 642.

Usui, N. (1996). Morphological differences in nuclear materials released from hamster sperm heads at an early stage of incorporation into immature oocytes, mature oocytes, or fertilized eggs. *Mol. Reprod. Develop,* 44, 132.

Perry, A.C.F. et al. (1999). Mammalian transgenesis by intracytoplasmic sperm injection. *Science* 284, 1180, May 14, 1999.

Hagmann, M. (1999). Fertility therapy may aid gene transfer. *Science* 284, 1097. May 14, 1999.

\* cited by examiner

SEQUENCE LISTING

<160> NUMBER OF SEQ ID NOS: 2

<210> SEQ ID NO 1
<211> LENGTH: 23
<212> TYPE: DNA
<213> ORGANISM: Artificial Sequence
<220> FEATURE:
<221> NAME/KEY: Left Primer - pCX-EGFP
<222> LOCATION:
<223> OTHER INFORMATION:
<300> PUBLICATION INFORMATION:
<301> AUTHORS: Perry, Anthony C.F.
      Wakayama, Teruhiko
      Kishikawa, Hidefumi
      Kasai, Tsuyoshi
      Okabe, Masaru
      Toyoda, Yutaka
      Yanagimachi, Ryuzo
<302> TITLE: Mammalian Transgenesis by
      Intracytoplasmic Sperm Injection
<303> JOURNAL: Science
<304> VOLUME: 284
<305> ISSUE:
<306> PAGES: 1180-1182
<307> DATE: 1999-05-14

<400> SEQUENCE: 1
ttgaattcgc caccatggtg agc                                    23

<210> SEQ ID NO 2
<211> LENGTH: 27
<212> TYPE: DNA
<213> ORGANISM: Artificial Sequence
<220> FEATURE:
<221> NAME/KEY: Right primer pCX-EGFP
<222> LOCATION:
<223> OTHER INFORMATION:
<300> PUBLICATION INFORMATION:

<400> SEQUENCE: 2
ttgaattctt acttgtacag ctcgtcc                                27

MAMMALIAN TRANSGENESIS BY INTRACYTOPLASMIC SPERM INJECTION This application claims the benefit of U.S. Provisional Patent Applications, Ser. No. 60/096,078, filed Aug. 11, 1998, and Ser. No. 60/133,970, filed May 13, 1999.

The U.S. Government has a paid-up license in this invention and the right in limited circumstances to require the patent owner to license others on reasonable terms as provided for by the terms of contract No. HD-34362 awarded by the National Institute of Child Health and Human Development.

BACKGROUND OF THE INVENTION

Transgenic animals are important for scientific, pharmaceutical and agricultural purposes. Production of foreign proteins in milk using genetically engineered livestock is believed to be a suitable system for making therapeutic recombinant proteins. Moreover, the insertion of human genes into the genomes of animals, such as pigs, could enable such animals to act as living organ or cell "factories" for human organs or cells that will not be rejected by the human immune system.

There are several reported methods of obtaining transgenic mammals by introducing foreign DNA into their somatic and germinal cells. One of these methods, pronuclear microinjection, has become widely used and was first developed in a mouse model in the early 1980s. Pronuclear microinjection entails injection of transgene (tg) DNA into a pronucleus of a one-cell embryo [J. W. Gordon, et al., Proc. Natl. Acad. Sci. U.S.A. 77, 7380 (1980); J. W. Gordon and F. H. Ruddle, Science 214, 1244 (1981); R. D. Palmiter and R. L. Brinster, Annu. Rev. Genet. 20, 465 (1986); and J. W. Gordon, Int. Rev. Cytol. 115, 171 (1989)]. Whereas the generation of pronuclear zygotes has been straightforward in the mouse, this is not necessarily true for species exemplified by the large commercial animal breeds. For example, zygotes are difficult substrates for pronuclear injection when their lipid richness renders them opaque, as in cattle and pigs; in contrast, mouse zygotes are translucent.

Transgenic embryonic stem (ES) cells, obtained by transfection with DNA constructs, have been used to obtain chimeric animals in cattle, sheep, and the like. This method involves the injection of genetically engineered ES cells harboring a desired mutation into fertilized embryos which are at the morula stage (about 20 to 50 cells) or the blastocyst stage (about 100 cells) of embryonic development. Upon implantation, such embryos often give rise to chimeric animals, whose subsequent breeding with wild-type animals results in germ line transmission of the ES cell-derived genome at variable frequencies (often equal to zero). Because the efficiency of gene transfer is low and because large numbers of recipient animals are required for embryo transfer, production of transgenic large animals by this method has been difficult.

Neither the pronuclear microinjection method nor the ES cell transfection method, described above, as yet permits the outcome of tg insertion to be controlled or predicted because the introduction of heterologous DNA into the cell often results in detrimental "position" or copy number effects caused by the quasi-random manner in which the transgene, or multiple copies thereof, integrate into the host genome (J. W. Gordon, supra). Therefore, the efficiency of these methods in producing transgenic large animals has been low.

It has been reported that greater control over the outcome of transgene integration can be achieved by using mouse ES cell lines transfected with DNA constructs capable of homologous recombination [M. J. Evans and M. H. Kaufman, Nature 292, 154 (1981); M. Kuehn, et al., ibid. 326, 295 (1987)]. These "gene targeted" ES cells are those in which one or more specific genes are knocked out or modified in a very precise manner that does not affect any other locus, genome-wide. "Immortalized" transgenic ES cell lines have been established and well characterized in vitro to confirm the construct integration site. However, gene targeting is currently restricted to the one species for which established, germline-contributing ES cell lines exist—the mouse.

Limitations in the available strategies for modifying mammalian germ lines have fueled a search for alternative methods, including the use of recombinant retroviruses to infect oocytes or preimplantation embryos [D. Jähner, et al., Proc. Natl. Acad. Sci. U.S.A. 82, 6927 (1985); A. W. S. Chan, et al., ibid., 95, 14028 (1998)] and the use of replication-deficient adenovirus-mediated delivery systems [Y. Kanegae, et al, Nucleic Acids Res. 23, 3816 (1995)]. However, viral protocols imply extra steps in cloning, necessitating specialized containment facilities for the recombinant adenoviruses and retroviruses that must be engineered. Delivery of the virus by these methods still requires either microinjection equipment or removal of the zona pellucida of the oocyte.

It has also been reported that spermatozoa may be used as vehicles for DNA delivery during in vitro fertilization (IVF) [M. Lavitrano, et al., Cell 57, 717 (1989)]. In this approach, live spermatozoa are used as a vector for introducing recombinant DNA into the oocyte in vitro. Although sperm-mediated DNA transfer to offspring has the potential to markedly simplify the generation of transgenic animals, there has been considerable controversy about the efficacy of the live spermatozoa method in promoting transgenesis because of its unreliability in consistently producing transgenic animals [M. Lavitrano, et al., 1989, supra; R. N. Brinster, et al., Cell 59, 239 (1989); B. Maione, et al., Mol. Reprod. Dev. 50, 406 (1998)]. In one report, exogenous DNA has been demonstrated to decorate intact spermatozoa in a reversible fashion [M. Lavitrano, et al., Mol. Reprod. Dev., 31, 161 (1992)], indicating that membrane structures may act as a barrier to the stable association of sperm heads with extraneous, recombinogenic DNA. In another report, live mouse spermatozoa incubated in vitro for two hours with a plasmid DNA showed some uptake of the exogenous DNA into the nucleus, as well as the plasma membrane. Sperm from the vas deferens into which plasmid DNA had been injected six hours previously, also showed some nuclear uptake. However, none of these spermatozoa were used to fertilize oocytes [E. Huguet and P. Esponda, Mol. Reprod. Dev. 51, 42 (1998)].

Therefore, there is still a need for an efficient transgene transfer method that can reliably be used to produce transgenic animals. More particularly, there is a need for an efficient method of obtaining genetically engineered livestock or other large animals for use as pharmaceutical "factories" and as a source of human organs or cells for xenotransplantation.

SUMMARY OF THE INVENTION

The invention provides a method for obtaining a transgenic embryo, comprising the steps of coinserting an exogenous nucleic acid and a membrane-disrupted sperm head or a demembranated sperm head into the cytoplasm of an unfertilized oocyte to form a transgenic fertilized oocyte, and allowing the transgenic fertilized oocyte to develop into a transgenic embryo and, if desired, into a live offspring. The coinserting step preferably comprises the substep of preincubating the membrane-disrupted or demembranated sperm head with the exogenous nucleic acid for a time period of about 30 seconds to about 5 minutes, typically about 45 seconds to about 3 minutes, more typically about 1 minute to about 2 minutes. The coinsertion of the sperm head and exogenous nucleic acid into the oocyte is by microinjection, preferably by piezo electrically-actuated microinjection. The exogenous nucleic acid mixed with the membrane-disrupted or demembranated sperm heads may comprise more than one transgene, to produce an embryo that is transgenic for more than one transgene.

Membrane-disrupted sperm heads suitable for use in the invention can be obtained from frozen-thawed spermatozoa or rehydrated freeze-dried spermatozoa. A method for preserving spermatozoa by freeze-drying and using the resulting reconstituted freeze-dried spermatozoa to fertilize oocytes in vitro to produce embryos and live offspring is the subject of our copending U.S. patent application, Ser. No. 09/177,391, filed Oct. 23, 1998, the disclosure of which is hereby incorporated by reference. Demembranated sperm heads suitable for use in the invention, comprising the nucleus and perinuclear materials, can be obtained by detergent-treatment of fresh spermatozoa, as described below.

The method of the invention may be used to produce transgenic embryos or live offspring of mammals, such as primates, ovines, bovines, porcines, ursines, felines, canines, equines and rodents. The method may also be used to produce transgenic invertebrates such as, but not limited to sea urchins, lobster, abalone or shell fish. The method may also be used to produce transgenic fish, amphibians, reptiles and birds. It has been discovered herein that live transgenic offspring (founder animals) produced by the process of the invention are themselves capable of producing transgenic offspring, showing stable integration of the tg into the founder genome and the fertility of the founders.

The method of mammalian transgenesis described herein contrasts with previous in vitro methods involving pronuclear injection of exogenous DNA into fertilized oocytes, or mixing live, intact spermatozoa with exogenous DNA and using these treated spermatozoa to fertilize oocytes to form transgenic embryos. The use of unfertilized metaphase II oocytes in the method of the invention represents a greatly simplified and facilitatory method over methods that require zygotes. Moreover, transgenesis by intracytoplasmic sperm injection (ICSI) may circumvent certain drawbacks to pronuclear microinjection. For example, the use of microinjection pipettes with about a 100-fold larger tip aperture (e.g., about 0.78 $\mu m^2$ for a pronuclear microinjection tip of diameter 1 $\mu m$, compared with about 78 $\mu m^2$ for an ICSI tip of diameter 10 $\mu m$) will facilitate the handling of large constructs, such as yeast or mammalian artificial chromosomes. Moreover, by the method of the invention, the association of the tg DNA with membrane-disrupted or demembranated sperm heads suggests the further stabilization and protection of megabase and sub-megabase constructs.

BRIEF DESCRIPTION OF THE DRAWINGS

FIG. 3(A–C) is a photomicrograph illustrating analysis of tail-tip biopsies from transgenic founders and nontransgenic controls.

DETAILED DESCRIPTION OF THE INVENTION

Figure 1:
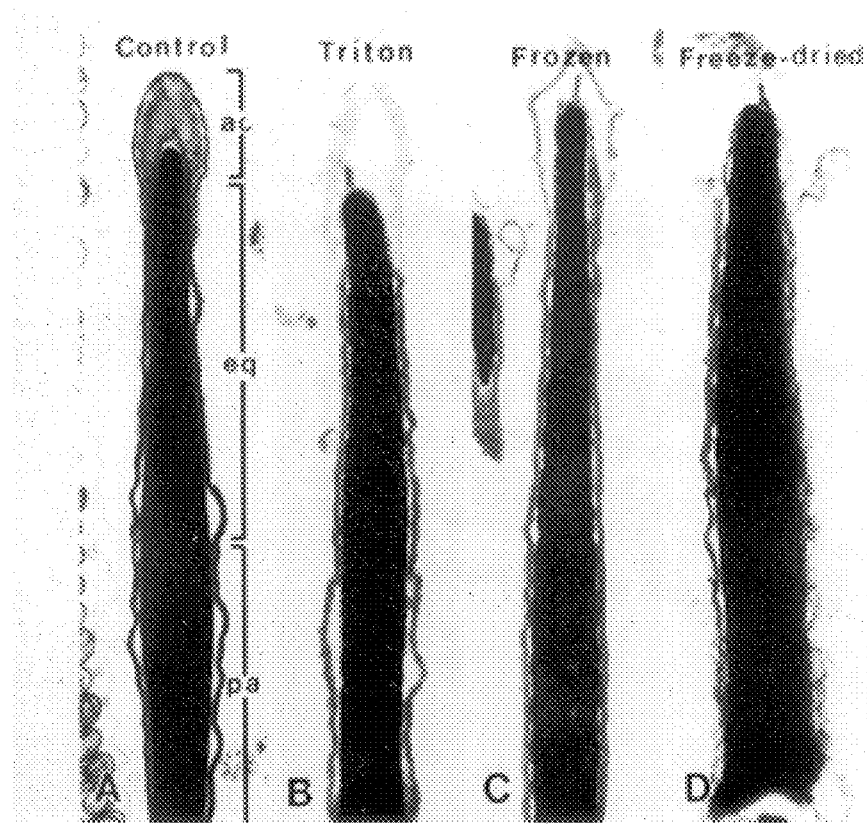
FIG. 1 is a photomicrograph illustrating representative sagittal sections through the heads of mouse spermatozoa that were either intact (fresh) (A) or whose membranes had been disrupted by Triton X-100 (B), freeze-thawing (C), or freeze-drying (D). ac, acrosomal cap; eq, equatorial segment; pa, postacrosomal region.

The invention provides methods for obtaining a transgenic embryo by coinserting an exogenous nucleic acid and a membrane-disrupted sperm head or a demembranated sperm head into an unfertilized oocyte. The method of the invention comprises the steps of: (i) obtaining a membrane-disrupted spermatozoon or a demembranated sperm head, (ii) mixing the membrane-disrupted spermatozoon or demembranated sperm head with an exogenous nucleic acid containing a desired gene, and (iii) coinserting the exogenous nucleic acid and the membrane-disrupted sperm head or demembranated sperm head into an isolated unfertilized oocyte to form a transgenic embryo expressing a desired transgene. The method may further comprise the step of implanting the transgenic embryo into the uterus of a surrogate mother and allowing the embryo to develop into a live transgenic offspring.

Embodiments of the individual steps and substeps of the methods of the invention are now presented in greater detail.
Preparation of Fresh Spermatozoa Fresh spermatozoa from invertebrates and vertebrates are collected by methods known to those skilled in the art. For example, mature spermatozoa of rodents, such as mouse, golden (Syrian) hamster, guinea pig, rabbit, and the like, may be collected from caudae epididymes; whereas, in other species, such as humans, pigs, horses, bulls, goats, fowl, and the like, mature spermatozoa may be isolated from freshly ejaculated semen of fertile males. Spermatozoa of fish (e.g., swordtail, *Xiphophorus helleri*) and invertebrates, such as sea urchins (*Tripneustes gratilla*), may be collected from the testes of mature males.

An example of a method for obtaining spermatozoa from a cauda epididymis follows. A cauda epididymis is removed from a mature male mouse (approximately 8 weeks after birth or older). The blood and adipose tissue are removed from the surface of the cauda epididymis. It is then compressed to release a dense mass of spermatozoa. A drop (about 2 microliters, $\mu l$) of sperm mass is placed in the bottom of 1.5 milliliter (ml) polypropylene centrifuge tubes and overlaid with 0.5 ml of warm physiological medium, such as CZB medium (the composition of which is described below), phosphate buffered saline, or isotonic saline. After about 10 to 20 minutes at 37° C., motile spermatozoa may be collected from the supernatant.

An example of a method for obtaining spermatozoa from semen follows. Freshly ejaculated human semen is allowed to liquefy for about 30 minutes at room temperature (about 25° C.). The semen is then diluted with about 10 ml of saline and filtered through about two layers of tissue paper to remove debris. The filtrate may then be centrifuged at 400×g for about 10 minutes, and the sedimented spermatozoa resuspended in a physiological solution at a desired concentration.

An example of a method for obtaining spermatozoa from testes follows. An excised testes is placed in an erythrocyte-lysing buffer (e.g., 155 millimolar (mM) $NH_4Cl$, 10 mM $KHCO_3$, 2 mM EDTA, pH 7.2–7.4), minced using a pair of fine scissors, and filtered through about two layers of tissue paper to remove debris. The filtrate is then centrifuged (e.g., 700×g, 5 minutes) and the pellet is resuspended in a physiological solution at a desired concentration.

Mouse spermatozoa so recovered, having intact plasma and acrosomal membranes are illustrated in FIG. 1(A), which is a photomicrograph of a representative sagittal sections through the head of a mouse spermatozoon where "ac" represents the acrosomal cap, "eq", the equatorial segment, and "pa", the postacrosomal region. The spermatozoa are suspended in a physiological medium, described below, in preparation for the freeze-thawing or freeze-drying process. Alternatively, the spermatozoa may undergo further processing to obtain demembranated sperm heads.

Preparation of Membrane-disrupted Spermatozoa
Membrane-disrupted Fresh Spermatozoa The membranes of fresh spermatozoa obtained as described above may be disrupted by mechanical means, such as by dislocation of sperm heads from tails in the microinjection pipette by the application of a single pulse from a piezo-electrically actuated microinjection unit, as described further below. As used herein, the term "fresh" spermatozoa refers to such membrane-disrupted spermatozoa for microinjection into unfertilized oocytes, and these are distinguished from, and represent a difference from, "live" spermatozoa used as vehicles for DNA delivery in previous reports of IVF.

Freeze-thawed Spermatozoa

Freezing and then thawing spermatozoa results in disruption of the plasma membrane, as assessed by viability staining techniques that are capable of distinguishing between plasma membrane-intact (live) and plasma membrane-damaged (dead) cells, as described in more detail below. Such freeze-thawed membrane-disrupted spermatozoa are considered "dead" in the conventional sense. Freeze-thawed spermatozoa may be prepared according to the methods described in T. Wakayama, et al., *J. Reprod. Fert.* 112, 11 (1996) and S. Kuretake, et al., *Biology of Reproduction* 55, 789 (1996). In particular, mouse epididymal spermatozoa suspended in CZB medium prior to cooling to −20° or −50° or −196° C. with or without cryoprotectants such as 18% (w/v) raffinose, and stored frozen for one to 28 days prior to thawing, supported the development of normal fertile live offspring when their heads were microinjected into unfertilized oocytes.

In the exemplary method for freezing mouse epididymal spermatozoa, the sperm concentration in CZB medium is about 3 to $10 \times 10^6$ per ml. An aliquot of 100 μl of the sperm suspension is transferred to a 1.5 ml polypropylene microcentrifuge tube (Fisher Scientific, Pittsburgh, Pa.) and mixed thoroughly with an equal volume of CZB medium, with or without 36% (w/v) D(+)-raffinose (giving a final concentration of 18% raffinose). A 50 μl aliquot of this suspension is dispensed into a labeled 1 ml cryogenic vial (A/S NUNC, Copenhagen). The vial is tightly capped and placed directly into a −20° C. or −50° C. freezer or liquid nitrogen (−196° C.). The sample may be stored for periods ranging from one day to four weeks.

For thawing, the vial is removed from the freezer or liquid nitrogen and placed in water or air at 24 to 26° C. for about ten minutes. The thawed sperm suspension is now ready for use in intracytoplasmic sperm injection (ICSI), as described below.

Although the method of obtaining freeze-thawed sperm has been described herein for mouse epididymal spermatozoa, one of ordinary skill in the art may adapt the method to spermatozoa from other vertebrates and invertebrates without undue experimentation.

Rehydrated Freeze-Dried Spermatozoa

Freeze-drying spermatozoa results in disruption of the plasma membrane, as assessed by viability staining techniques that are capable of distinguishing between plasma membrane-intact (live) and plasma membrane-damaged (dead) cells (described below). Such freeze-dried membrane-disrupted spermatozoa are considered "dead" in the conventional sense. Freeze-dried spermatozoa may be prepared according to the methods described in T. Wakayama and R. Yanagimachi, *Nature Biotechnology* 16, 639, (1998) and in our copending U.S. patent application, Ser. No. 09/177,391, filed Oct. 23, 1998. In particular, the patent application discloses general methods that may be used for freeze-drying spermatozoa from vertebrates and invertebrates. In an exemplary method, mouse epididymal spermatozoa suspended in (1) CZB medium without ethylenediamine tetraacetic acid (EDTA) containing 4 mg/ml BSA, or (2) Dulbecco's modified Eagle's medium (DMEM) supplemented with 10% (v/v) fetal bovine serum (Hyclone, Logan, Utah) prior to freezing in liquid nitrogen and drying to a water content of near zero percent, and stored freeze-dried for up to six months prior to rehydrating, supported the development of normal fertile live offspring when they were rehydrated and their heads were microinjected into unfertilized oocytes.

In the exemplary method for freezing mouse epididymal spermatozoa, the sperm concentration in the CZB or DMEM medium is about 3 to $10 \times 10^6$ per ml. An aliquot (100 μl) of the sperm suspension is put in a 2 ml ampule (Wheaton Scientific, Millville, N.J., Catalogue No. 651506) which is plunged directly into liquid nitrogen. Ten minutes later, ampules are placed in a pre-cooled (−50° C.) freeze-flask attached to a freeze-dry system (Model 10-020, VirTis Co., Gardner, N.Y.). The inlet pressure is approximately 1 milliTorr. About 12 hours later, the flask is removed from the system after it has been filled with argon supplied by way of a gas-drying jar (Fisher Scientific, Pittsburgh, Pa. Catalogue No. 09-204). Each ampule is connected to a vacuum pump and frame-sealed after more than greater than 99% of the gas is pumped out of it. Ampules are individually wrapped with aluminum foil and stored in the dark at room temperature (about 25° C.) or at 4° C. for up to a year prior to use.

For rehydration of the foregoing freeze-dried sperm, an ampule containing freeze-dried sperm prepared as above is broken and 100 μl of distilled water are added to the ampule to form a reconstituted sperm suspension.

Although the method of obtaining rehydrated freeze-dried sperm has been described herein for mouse epididymal spermatozoa, one of ordinary skill in the art may adapt the method to spermatozoa from other vertebrates and invertebrates without undue experimentation, as taught in U.S. patent application, Ser. No. 09/177,391.

It has been noted that the incidence of oocyte activation and normal fertilization following sperm head injection appears to decrease with increasing time after rehydration of freeze-dried sperm. The allowable time period between rehydration and injection may vary between species; however, as an example, this time period for mouse spermatozoa is preferably one hour or less.

Preparation of Demembranated Sperm Heads

Demembranated sperm heads are detergent-extracted heads that lack all membranes, including the plasma membrane and inner and outer acrosomal membranes, but retain the nucleus and perinuclear material. For example, sperm heads may be demembranated by treatment with Triton X-100 with or without SDS (sodium dodecyl sulfate). Triton X-100 is a well known non-ionic surfactant that is widely used for removal of membrane components under non-denaturing conditions. SDS is an anionic detergent used to solubilize various proteins, including membrane proteins. In the mouse, sperm heads demembranated by using Triton X-100 have been shown to be capable of activating oocytes, leading to normal embryonic development.

An exemplary method for demembranating sperm heads follows. An aliquot of a sperm suspension, prepared as above, is sonicated. For example, spermatozoa collected from caudae epididymes, testes or semen, as above, may be suspended in 5 ml BM buffer (75 mM NaCl, 24 mM EDTA, and 50 mM Tris-HCl, pH 7.2) and sonicated for 30 seconds at 70%–80% output of a Biosonik sonicator (Bronwill Scientific, Rochester, N.Y.). Over 95% of spermatozoa are decapitated by this treatment. To demembranate the sperm heads, the sonicated sperm suspension is centrifuged at 700×g for 5 minutes, and the pellet is washed with BM buffer and then treated at room temperature for 5 minutes with 1% Triton X-100 in NIM medium. (NIM medium consists of 123.0 mM KCl, 2.6 mM NaCl, 7.8 mM $NaH_2PO_4$, 1.4 mM $KH_2PO_4$, 3 mM $Na_2EDTA$, having a pH of 7.2). The heads are then rinsed thoroughly with NIM medium and resuspended in sperm suspension medium.

Assessment of Sperm Viability

The photomicrograph of FIG. 1(B), (C) and (D), representing longitudinal cross-sections through the anterior region of the sperm heads, shows that the plasma and acrosomal membranes, except for those in the equatorial region, are absent or disrupted in spermatozoa treated by Triton X-100 (detergent) (B), freeze-thawing (C) or freeze-drying (D).

Viability of the spermatozoa may be assessed by using any staining method that is capable of distinguishing between spermatozoa that are, in the conventional sense, live or dead. A suitable commercially available viability test kit for use in the invention is Live/dead FertiLight, available from Molecular Probes, Eugene, Oreg., which differentiates between plasma membrane-intact (live) and plasma membrane-damaged (dead) cells according to a fluorescence pattern under an ultraviolet (UV) microscope after staining with propidium iodide/SYBR 14. The nuclei of "live" spermatozoa with intact plasma membranes fluoresce green, whereas those of "dead" spermatozoa fluoresce bright orange-red. It is expected that all of the spermatozoa prepared by physical membrane disruption, or by the freeze-thawing, freeze-drying and demembranation procedures, described above, will be "dead" in the conventional sense.

Selection and Preparation of Exogenous Nucleic Acid Containing a Transgene

Genetic transformation, according to the invention, is the stable integration of an exogenous foreign DNA into the genome of a zygote, and includes integration of the foreign DNA into host cell nuclear DNA and/or extranuclear DNA in mitochondria. Foreign DNA is genetic material that is not indigenous to (not normally resident in) the zygote before transformation or is not normally present in more than one copy. However, "foreign" DNA may include a further copy of an indigenous gene or genetic sequence that is introduced for purposes of co-suppression.

The foreign genetic material may comprise DNA from any origin including, but not limited to, plants, bacteria, viruses, bacteriophage, plasmids, plastids, mammals and synthetic DNA constructs. The DNA may be in circular or linear form and may be single-stranded or double-stranded. The DNA may be inserted into the host cell DNA in a sense or anti-sense configuration and in single-stranded or double-stranded form. All or part of the DNA inserted into the host cell may be integrated into the genome of the host.

Selection and/or synthetic construction of plasmids and other cloning vectors containing specific genes are well known in the art. Synthetic constructs of chimeric plasmids contain the gene or gene of interest and frequently comprise promoter and/or leader sequences obtained from diverse sources to facilitate insertion into the host genome. Although prokaryotic cloning vector sequences have no apparent effect on the integration frequency of microinjected genes, it has been noted that they can severely inhibit the expression of eukaryotic genes introduced into a germ line of a manunal, such as a mouse [see B. Hogan, et al., in Manipulating the Mouse Embryo, Section E, Second Ed., Cold Spring Harbor Laboratory Press, p. 22 (1994)]. Therefore, it may be advisable to remove substantially all vector sequences from a cloned gene before introducing it into the germ line of a mammal, such as a mouse, if optimal expression of the gene is desired. Vector sequences may be removed by employing restriction enzymes, according to the restriction sites present on the vector, by methods known to those skilled in the art, to produce fragments containing the desired gene, promoters, enhancers, and the like.

The level of expression of the introduced gene depends mostly on the strength of the promoter and the copy number of the integrated DNA in the transfected cells. Therefore, expression vectors utilize very strong promoters, such as the SV40 early or late promoter, the cytomegalovirus immediate early (CMV-IE) promoter, the cytoplasmic β-actin promoter, and the adenovirus major late promoter.

The successful delivery of the DNA into a cell may be preliminarily evaluated by the expression of a "reporter" gene. A reporter gene is a component of the DNA used for transformation and may be the same as or different than the transgene conferring another desired property. The property conferred on the transformed cell or tissue by the reporter gene is usually easily detectable by histochemical or fluorescence assays. There are a number of commonly used in vitro reporter genes for quantifiing transfection efficiencies, and numerous plasmids and cloning vectors containing reporter transgenes are available from commercial sources, known to those skilled in the art, such as Sratagene, Inc., LaJolla, Calif., and Clontech Laboratories, Inc., Palo Alto, Calif. Exemplary reporter genes for use in the present invention include, but are not limited to, secreted alkaline phosphatase [SEAP; β-galactosidase (β-gal); firefly luciferase, and chloramphenicol acetyltransferase (CAT)]. In vivo reporter assays, such as in situ β-gal staining, in situ β-glucuronidase [GUS] and in situ luciferase assays are also available for detecting gene transfer in either fixed cells or tissue sections. These procedures allow visualization of transfected cells following staining with enzymatic substrates or antibodies. Among these procedures, in situ β-gal staining following expression of the *Escherichia coli* LacZ gene is a widely used method because of its simplicity and sensitivity. In this procedure, reaction of β-gal with the X-gal substrate produces a rich blue color that can be easily visualized under a light microscope and, there, provides a direct assessment of transfection efficiency.

The green fluorescent protein (GFP) from the jellyfish *Aequorea victoria* has become an important reporter for monitoring gene expression and protein localization in a variety of cells and organisms [R. Y. Tsien, *Annu. Rev. Biochem.* 67, 509 (1998); G. Zhang, et al., *Biochemical and Biophysical Research Communications* 227, 707–711 (1996); T. Takada, et al., *Nature Biotechnology* 15, 458–460, (1997) ]. Because GFP does not require any substrate for detection, it can be a suitable marker for the selection of transgenic embryos. GFP expressed in eukaryotic cells yields green fluorescence when cells are excited by UV or blue light. The chromophore in GFP is intrinsic to the primary structure of the protein, and fluorescence from GFP does not require additional cofactors, substrates, or additional gene products. GFP fluorescence is stable, species-independent, and can be monitored noninvasively using techniques of fluorescence microscopy, flow cytometry, and macroscopic imaging. To increase the fluorescent intensity of GFP when excited by blue light, an enhanced GFP (EGFP) variant has been constructed (pEGFP-Cl available from Clontech Laboratories) that contains the immediate early promoter of human CMV and SV40 polyadenylation signals to drive expression of the EGFP gene in mammalian cells.

Mixing of Spermatozoa with Vector Fragment Containing a Desired Transgene

Spermatozoa prepared as above may be mixed with the vector fragment without further preparation (fresh) or after they are subjected to one of the three membrane-disruption protocols, described above. In a typical mixing procedure, 1 $\mu$l of a DNA solution containing a vector fragment (about 2.5 ng/$\mu$l) is mixed with 9 $\mu$l of a suspension containing about 2 to $5\times10^5$ spermatozoa in a physiological medium, such as CZB or NIM, and mixed by pipetting to give a final DNA fragment concentration of 7 ng/$\mu$l. The mixture is incubated at room temperature (about 25° C.) or on ice for about 30 seconds to about 5 minutes, typically about 45 seconds to about 3 minutes, more typically about one to about 3 minutes, preferably about one minute. The concentration of sperm and DNA fragments may be varied, as well as the incubation times and temperatures, depending on the size of the fragment, or the size of the sperm, and the like, as known to those skilled in the art.

Microinjection of the mixture of spermatozoa and DNA fragment is usually carried out at room temperature within one hour of sperm-DNA mixing or within one hour of sperm demembranation.

The Recipient Oocytes

Recipient oocytes that may be used in the method of the invention include both immature (e.g., GV stage) that are subsequently matured in vitro, and mature (i.e., Met II stage) oocytes that have been harvested from an animal. Mature oocytes may be obtained, for example, by inducing an animal to superovulate by injections of gonadotrophic or other hormones (for example, sequential administration of equine and human chorionic gonadotrophin) and surgical harvesting of ova shortly after ovulation (e.g., 80 to 84 hours after the onset of estrous in the domestic cat, 72 to 96 hours after the onset of estrous in the cow and 13 to 15 hours after the onset of estrous in the mouse). Where it is only possible to obtain immature oocytes, they are cultured in a maturation-promoting medium until they have progressed to Met II; this is known as in vitro maturation ("IVM"). Methods for IVM of immature bovine oocytes are described in WO 98/07841, and for inunature mouse oocytes in Eppig & Telfer (*Methods in Enzymology* 225, 77–84, Academic Press, 1993).

The stage of in vivo maturation of the oocyte at fertilization has been previously reported to be significant to the success of in vitro nuclear transfer methods for producing embryos. It is known that the chemistry of the oocyte cytoplasm changes throughout the maturation process. For example, a cytoplasmic activity associated with maturation, metaphase-promoting factor ("MPF"), is high in immature oocytes at metaphase of the first meiotic division, declining with the formation and expulsion of the first polar body, and again reaching high levels at Met II. MPF activity remains high in oocytes arrested at Met II, rapidly diminishing upon oocyte activation. In general, reports of mammalian nuclear transfer describe the use of Met II oocytes as recipients. Met II oocytes are of the type ready to be activated by fertilizing spermatozoa. When a cell nucleus is introduced into the cytoplasm of an unfertilized Met II oocyte (i.e., one with high MPF activity), the nuclear envelope (if it has one) of the cell breaks down and chromatin condenses, resulting in the formation of metaphase chromosomes.

Recipient oocytes are surgically harvested from oviducts as oocyte-cumulus cell complexes and placed in a buffered medium, such as Hepes-CZB medium (described below). Cumulus cells are dispersed with a dispersing enzyme, such as 0.1% bovine testicular hyaluronidase (e.g., 300 USP units/mg, ICN Pharmaceuticals, Costa Mesa, Calif.). It is preferred that cumulus-free oocytes are kept in a medium, such as CZB medium equilibrated in 5% (v/v) $CO_2$ in air, at 37.5° C., under mineral oil (such as that available from E. R. Squibb and Sons, Princeton, N.J.) for less than one hour before further treatments.

Sperm Components Necessary for Successful in Vitro Fertilization

It is known that, in the mouse, normal fertilization can be achieved by injecting isolated sperm heads into oocytes, and that the plasma and acrosomal membranes and all tail components are not essential for normal embryo development. The mouse and, perhaps, most common laboratory rodents are "exceptional" in that a sperm centrosome is not required for normal fertilization and, during normal fertilization, the sperm centrosome in the neck region of the spermatozoon is destined to degenerate within the oocyte after fertilization.

In contrast, in most other eutherian mammals, including cattle and humans, the sperm centrosome plays a central role in the formation of the microtubules which are essential for the union of male and female pronuclei, as well as in the subsequent cleavages during embryonic development. Therefore, in these species, the introduction of both a sperm nucleus (head) and a centrosome into an oocyte seems to be essential for the production of normal offspring. It is not known at this time whether the sperm centrosome from all species can survive freeze-thawing, freeze-drying or demembranation by detergents. If not, a centrosome from an unfrozen sperm must be injected into an oocyte together with the freeze-thawed, freeze-dried or demembranated sperm head in order to secure normal embryonic development. Introduction of excessive numbers of centrosomes, however, would result in abnormal pronuclear development and abnormal embryonic development.

The centrosome is normally attached either to the posterior end of the sperm head or to the anterior end of the sperm tail when the head and tail are separated. Thus, the sperm centrosome may be inserted into the oocyte simultaneously with the sperm head, or may be inserted by means of simultaneous or consecutive insertion of a sperm tail.

Insertion of Spermatozoa Nucleus into Recipient Oocyte

The entire spermatozoon can be coinjected with the exogenous nucleic acid into the cytoplasm of the recipient oocyte, but in species in which the spermatozoa are large, an isolated sperm head (nucleus) is preferably injected directly into the cytoplasm of a recipient oocyte by a microinjection technique. In a preferred method of micro-coinjection of the exogenous nucleic acid with a freeze-thawed, rehydrated freeze-dried sperm head or demembranated sperm head into a recipient oocyte, the piezo electrically-driven micropipette is used.

A suitable piezo electric driving unit is sold under the name of Piezo Micromanipulator/Piezo Impact Drive Unit by Prime Tech Ltd. (Tsukuba, Ibaraki-ken, Japan). The unit utilizes the piezo electric effect to advance, in a highly controlled, rapid manner, the (injection) pipette holder a very short distance (approximately 0.5 $\mu$m). The intensity and duration of each pulse can be varied and are regulated by a control unit.

For injection into an oocyte, a single spermatozoon, in the mixture of the sperm/sperm heads and exogenous nucleic acid, is aspirated tail first (if it has a tail) into an injection pipette having a short, flat tip with an inner diameter of about 5 $\mu$m housed in the piezo electrically-actuated unit according to the instructions of the vendor. The sperm head and tail are separated by applying a single or a few Piezo pulses to the neck region. The head is then drawn deeply into the pipette. Alternatively, as single sperm head in the mixture of sperm/sperm heads and exogenous nucleic acid may be aspirated into the injection pipette, for injection into an oocyte.

Throughout the coinjection of the sperm head (nucleus) and exogenous nucleic acid, the oocyte is anchored by a conventional holding pipette. The tip of the injection pipette containing a selected sperm head is brought into intimate contact with the zona pellucida of an oocyte and several piezo pulses (using controller setting scales of intensity 1–5, speed 4–6) are applied to advance the pipette while maintaining a light negative pressure within. When the tip of the pipette has passed through the zona pellucida, the resultant zona plug is expelled into the perivitelline space and the sperm head is pushed forward until it is near the tip of the pipette. The pipette tip is then apposed to the plasma membrane and advanced (toward the opposite face of the oocyte) and the holding pipette almost reaches the opposite side of the cortex of the oocyte. The oocyte plasma membrane is now deeply invaginated around the tip of the injection needle. Upon application of one to two piezo pulses (intensity 1–2, speed 1), the oolemnma is punctured at the pipette tip, as indicated by a rapid relaxation of the oolemma, which may be clearly visible. The sperm head is then expelled into the ooplasm with a minimum amount (about 6 pl) of accompanying medium containing the exogenous nucleic acid. The pipette is then gently withdrawn, leaving the newly introduced head within the cytoplasm of the oocyte. This method is performed briskly, typically in batches of 10–15 oocytes which at all other times are maintained in culture conditions.

Alternative microinjection variants, in which a conventional injection pipette is employed, may be used for the coinjection procedure. An example of a suitable microinjection method employing a conventional pipette, for injecting a sperm head into hamster oocyte, is described in Yanagida, K., Yanagimachi, R., Perreault, S. D. and R. G. Kleinfeld, *Biology of Reproduction* 44, 440–447 (1991), the disclosure of which pertaining to such method is hereby incorporated by reference.

Micro-coinjection of the exogenous nucleic acid and spermatozoon/sperm head/demembranated sperm head offers several advantages. First, spermatozoon/sperm head delivery by microinjection is applicable to a wide variety of spermatozoa types, irrespective of size, morphology, and the like. Second, microinjection allows carefully controlled co-injection (with the donor spermatozoon/sperm head) of other agents, in addition to the exogenous nucleic acid described above, into the oocyte at the time of injection. These are exemplified below. Third, in the embodiment of the invention wherein insertion of the spermatozoon/sperm head is by piezo electrically-actuated microinjection, rapid and efficient processing of samples is afforded, thereby reducing trauma to sperm and oocytes undergoing manipulation. The oocytes of some species (e.g., mouse) are not amenable to microinjection using conventional needles, whereas piezo electrically-actuated microinjection affords a high success rate.

Activation of Fertilized Oocytes

It is known that the mouse oocyte can be activated by injection of a single, intact mouse spermatozoon or its isolated head. Isolated sperm tails are unable to activate the oocyte. Active sperm-borne oocyte-activating factor(s) typically appear during transformation of the round spermatid into the spermatozoon. The action of these factors is not highly species-specific because mouse oocytes are activated by injection of spermatozoa from foreign species, such as the hamster, rabbit, pig, human and even fish. It has been reported that one such activating factor is a 33 kilodalton protein residing in the equatorial segment region of the acrosome. This protein, called oscillin, is readily extractable from mature (hamster) spermatozoa by simple freezing and thawing. Besides oscillin, mature spermatozoa appear to carry another activating factor that is not readily extractable, but may be obtained by sequential treatment of spermatozoa with Triton X-100 and SDS. It is not known whether the readily extractable oscillin and the freeze/thaw extraction-resistant factors are biologically and chemically identical.

It is known that sperm heads sonicated in the presence of Triton X-100 lose all components but the nucleus and perinuclear materials. Yet, when microsurgically injected into oocytes, such Triton X-100-treated sperm heads (having the nucleus and perinuclear materials, but no plasma membranes) can activate oocytes as efficiently as intact spermatozoa.

As described in the our copending U.S. patent application, Ser. No. 09/177,391 and in T. Wakayama, et al., 1997, supra, at least in the mouse, sperm-borne oocyte-activating molecules must be resistant to freeze-thawing and freeze-drying because the majority of the oocytes that survived the injection of freeze thawed or freeze-dried sperm heads were activated and fertilized normally.

If in other species the injection of the sperm head does not serve to activate the oocyte, activation may take place by parthenogenetic means, such as by electroactivation, injection of one or more oocyte-activating substances, or transfer of the oocytes into media containing one or more oocyte-activating substances. Reagents capable of providing an activating stimulus (or combination of activating stimuli) include, but are not limited to, sperm cytoplasmic activating factor, and certain pharmacological compounds (e.g., $Ca^{2+}$ and other signal transduction modulators), which may be introduced by microinjection after, or concomitantly with, coinjection of the sperm head and exogenous nucleic acid. Some activating stimuli are provided following transfer of the fertilized oocytes to media containing one or members of a sub-set of activating compounds, including stimulators of $Ca^{2+}$ release (e.g., caffeine, $Ca^{2+}$ ionophores such as A 23187 and ionomycin, and ethanol), modulators of phosphoprotein signaling (e.g., 2-aminopurine, staurospurine, and sphingosine), inhibitors of protein synthesis (e.g., A 23187, cycloheximide), 6-dimethylaminopurine, or combinations of the foregoing (e.g., 6-dimethylaminopurine and ionomycin). In an exemplary method, activation of mouse oocytes is achieved by culture for 1–6 hours in $Ca^{2+}$-free CZB medium containing 2 to 10 mM $Sr^{2+}$.

Development of Embryos to Produce Viable Fetuses and Offspring

Following pronucleus formation, the embryo may be cultured in vitro until it reaches the 2–8 cell stage or morula/blastocyst stage, at which time the embryo may be transferred into the oviduct or uterus of a foster mother.

Simultaneous Injection of Biologically Interesting Substances with Sperm Heads

In one embodiment of the invention, micro-coinjection of the sperm head and exogenous nucleic acid into an oocyte permits the introduction, prior to, during, or after the injection of the sperm head into the oocyte, of one or more agents with the potential to alter the developmental outcome of the embryo. For example, an additional ribonucleic acid (RNA) or DNA may be introduced into the oocyte by microinjection prior to or following coinjection of the sperm head and exogenous nucleic acid. For example, injection of recombinant DNA harboring cis-active signals may result in the transcription of sequences present on the recombinant DNA by resident or co-injected transcription factors, and subsequent expression of encoded proteins with an antagonistic effect on development inhibitory factors, or with a positive effect on embryo development. Moreover, the transcript may possess antisense activity against mRNAs encoding development inhibitory proteins. Alternatively, antisense regulation may be achieved by injecting nucleic acids (or their derivatives) that are able to exert an inhibitory effect by interacting directly with their nucleic acid target(s) without prior transcription within the oocyte.

Recombinant DNA (linear or otherwise) introduced by the method of the invention may comprise a fumctional replicon containing one or more expressed, functional gene under the control of a promoter exhibiting anything from a narrow to a broad developmental expression profile. For example, the promoter might direct immediate, but brief expression where that promoter is active only in the early zygote. Introduced DNA may either be lost at some point during embryonic development, or integrate at one or more genomic loci, to be stably replicated throughout the life of the resulting transgenic individual. In one embodiment, DNA constructs encoding putative "anti-aging" proteins, such as telomerase or superoxide dismutase, may be introduced into the oocyte by microinjection. Alternatively, such proteins may be injected directly.

EXAMPLES

To illustrate the method of the invention, the ability of the membrane-disrupted and/or demembranated spermatozoa to transfer into an unfertilized oocyte a replication-deficient fragment of a plasmid containing an expressed reporter gene, and the development of transgenic mouse embryos and live transgenic offspring therefrom, was evaluated. The use of a reporter gene enabled the direct identification of embryos and live offspring expressing the transgene.

The examples described herein are not intended to be limiting, as one skilled in the art would recognize that other transgenes, spermatozoa and oocytes from sources other than the mouse, and other physiological media or reagents may be used in the method of the invention.

Media and Reagents

All inorganic and organic compounds were purchased from Sigma Chemical Co. (St. Louis, Mo.) unless otherwise stated.

Harvested oocytes were kept in CZB medium (Chatot, et al., 1989. *J. Reprod. Fert.* 86, 679–688) prior to coinjection of exogenous DNA and membrane-disrupted sperm or demembranated sperm heads. CZB medium comprises 81.6 mM NaCl, 4.8 mM KCl, 1.7 mM $CaCl_2$, 1.2 mM $MgSO_4$, 1.8 mM $KH_2PO_4$, 25.1 mM $NaHCO_3$, 0.1 mM $Na_2EDTA$, 31 mM Na.lactate, 0.3 mM Na.pyruvate, 7 U/ml penicillin G, 5 U/ml streptomycin sulfate, and 4 mg/ml bovine serum albumin (BSA). The medium for oocyte collection from oviducts, subsequent treatments and micromanipulation was a modified CZB containing 20 mM Hepes, a reduced amount of $NaHCO_3$ (5 mM) and BSA (3 mg/ml). This medium is herein termed Hepes-CZB. For microinjection purposes, it was preferred to replace the BSA in the Hepes CZB with 0.1 mg/ml polyvinyl alcohol (PVA, cold water soluble, average molecular mass $10 \times 10^3$) because PVA kept the wall of the injection pipette less sticky over a longer period of time than BSA and was beneficial during repeated use of a single pipette for multiple sperm head/oocyte transfers. The pH of both media was approximately 7.4. All oocyte manipulations were carried out in Hepes-buffered CZB (Hepes-CZB) under mineral oil at room temperature (23° to 25° C.) in air.

The medium used for isolation of fresh spermatozoa was CZB medium. Freeze-thawed and rehydrated freeze-dried spermatozoa were suspended in either CZB medium or nuclear isolation medium (NIM) consisting of 123.0 mM KCl, 2.6 mM NaCl, 7.8 mM $NaH_2PO_4$, 1.4 mM $KH_2PO_4$, 3 mM $Na_2EDTA$. Its pH value was adjusted to 7.2 by addition of a small quantity of 1 M HCl. Fresh spermatozoa for demembranation were harvested in NIM and also treated by Triton X-100 extraction in NIM. After washing, the demembranated sperm heads were suspended in NIM or CZB medium. After incubation of the sperm (in CZB or NIM) with exogenous DNA, the mixture was supplemented with PVP (average molecular mass 360,000, ICN Biochemicals, Costa Mesa, Calif.).

Animals

Animals used in these examples were maintained in accordance with the guidelines of the Laboratory Animal Service at the University of Hawaii and those prepared by the Committee on Care and Use of Laboratory Animals of the Institute of Laboratory Resources National Research Council (DHEW publication no. [NIH] 80-23, revised in 1985). The protocol of animal handling and treatment was reviewed and approved by the Animal Care and Use Committee at the University of Hawaii.

Example 1

Oocyte Preparation

Mature B6D2F1 (C57BL/6X DBA/2) female mice were induced to superovulate by consecutive injections of 7.5 International Units (IU) pregnant mare serum gonadotropin and 7.5 IU human chorionic gonadotropin (hCG) 48 hours apart. Fourteen hours after hCG injection, cumulus-oocyte complexes were collected from oviducts and treated with bovine testicular hyaluronidase (300 USP U/ml; ICN Biochemicals, Costa Mesa, Calif.) in Hepes-CZB medium for 3 minutes to disperse cumulus cells. Prior to injection with sperm nuclei, the oocytes were rinsed and stored in CZB medium under mineral oil equilibrated in 5% (v/v) $CO_2$ in air, at 37° C., for up to 4 hours

Example 2

Preparation of Fresh Spermatozoa

Fresh spermatozoa were collected from the caudae epididymes of B6D2F1 male mice. While applying finger pressure o each epididymis, its distal portion was punctured with sharp forceps. A dense sperm mass oozing out of the epididymis was transferred to a petri dish. Drops (about 2 $\mu$l) of spermatozoa were placed in the bottom of 1.5 ml polypropylene microcentrifuge tubes (Fisher Scientific, Pittsburgh, Pa.) and overlaid with 0.2 to 0.5 ml CZB medium. After incubation of about 20 min, the upper 0.4 ml of medium was collected and examined. Over 90% of the spermatozoa in the suspension (approximately 3 to $10 \times 10^6$ per ml) were actively motile.

Example 3

Preparation of Freeze-thawed Spermatozoa

Freeze-thawed spermatozoa were prepared according to the method described in T. Wakayama, D. G. Whittingham and R. Yanagimachi, *J. Reprod. Fert.*, 112, 11–17, 1998. Briefly, drops of spermatozoa obtained from the cauda epididymis were placed in the bottom of 1.5 ml polypropylene centrifuge tubes and overlaid with 0.5 ml warm CZB. After about 20 min at 37° C., the upper 0.2 ml of medium was collected. The suspension contained approximately 3 to $10 \times 10^6$ sperm per ml. An aliquot (100 $\mu$l) of the sperm suspension was transferred to a 1.5 ml polypropylene microcentrituge tube and mixed thoroughly with an equal volume of CZB medium, with or without 36% (w/v) D(+)-raffinose. The final concentration of raffinose was 18% or 0% (w/v), respectively. Aliquots (50 $\mu$l) of each suspension were dispensed into labeled 1 ml cryogenic vials (A/S NUNC, Copenhagen). Each vial was tightly capped and placed directly into a –20° C. or –50° C. freezer or liquid nitrogen (–196° C.). All samples were st periods ranging from one day to four weeks.

For thawing, vials were removed from the freezer or liquid nitrogen and placed in water or air at 24–26° C. for about 10 min. A sample of the thawed sperm suspension was examined for motility and "viability" by a commercially available sperm viability test kit (Live/dead FertiLight, Molecular Probes, Inc., Eugene, Oreg.), as described herein above. All spermatozoa frozen in the absence of raffinose were non-motile and "dead" (membrane disrupted). At least 97% of spermatozoa frozen in the present of raffinose at any temperature were non-motile and "dead".

The thawed sperm suspension was washed once and resuspended in 400 $\mu$l CZB medium prior to mixing with exogenous DNA.

Disruption of the membranes was confirmed by electron microscopy, as illustrated in FIG. 1(C). Disruption is clearest in the membranes of the acrosomal cap.

Example 4

Preparation of Rehydrated Freeze-dried Spermatozoa

Rehydrated freeze-dried spermatozoa were prepared according to the methods described in T. Wakayama and R. Yanagimachi, *Nature Biotechnology* 16, 638–640, 1998, and in our copending U.S. patent application, Ser. No. 09/177, 391. Briefly, an aliquot (100 $\mu$l) of the suspension of mouse spermatozoa, prepared as described above, was transferred to a 1.5 ml polypropylene microcentrifuge tube and mixed thoroughly with one ml of either CZB medium without EDTA containing 4 mg/ml BSA, or Dulbecco's modified Eagle's medium (DMEM) supplemented with 10% (v/v) fetal bovine serum (Hyclone, Logan, Utah). After incubation for 30 minutes at 37.5° C., the upper 0.3 to 0.5 ml of the medium was removed from the tube. The suspension contained approximately 3 to $10 \times 10^6$ sperm per ml.

An aliquot (100 $\mu$l) of the sperm suspension was put in a 2 ml ampule (Wheaton Scientific, Millville, N.J.), which was plunged directly into liquid nitrogen. Ten minutes later, ampules were placed in a precooled (–50° C.) freeze-flask attached to a freeze-dry system (Model 10-020, VirTis, Gardner, N.Y.). The inlet pressure was approximately 1 milliTorr. About 12 hours later, the flask was removed from the system after it had been filled with argon supplied by way of a gas-drying jar (Fisher Scientific, Pittsburgh, Pa., Catalogue No. 09-204). Each ampule was connected to a vacuum pump and frame-sealed after more than greater than 99% of the gas was pumped out of it. Ampules were individually wrapped with aluminum foil and stored in the dark at room temperature (about 25° C.) or at 4° C.

For rehydration, an ampule containing freeze-dried sperm prepared as above was broken and 100 $\mu$l of distilled water were added to the ampule to form a reconstituted sperm suspension.

Disruption of the membranes was confirmed by electron microscopy, as illustrated in FIG. 1(D). Disruption is clearest in the membranes of the acrosomal cap.

Example 5

Preparation of Demembranated Sperm Heads

Spermatozoa for Triton X-100 extraction were isolated by finely chopping two caudae epididymes at 0° to 1° C. in NIM medium, and filtering the resulting sperm suspension to produce a final volume of 900 $\mu$l. For Triton X-100 extraction, 100 $\mu$l of 0.5% (v/v in NIM) of Triton X-100 was added to the 900 $\mu$l of sperm suspension in NIM and mixed by trituration for 30 seconds on ice. Cells were pelleted by centrifugation for 1 min. at 20,000×g at 2° C., and thoroughly resuspended in 2 ml of ice-cold NIM before repelleting for 2 min at 20,000×g at 2° C. The final pellet was resuspended in 400 $\mu$l of CZB or NIM.

Demembranation of the sperm heads was confirmed by electron microscopy, as illustrated in FIG. 1((B). Disruption is clearest in the membranes of the acrosomal cap.

Example 6

Preparation of Transgenes

The enhanced green fluorescent protein (EGFP) transgene was a large (3.5 kb) Sal GI-Bam HI fragment of plasmid pCX-EGFP. The fragment harbors an EGFP gene expressed from a strong cytomegalovirus-IE-chicken β-actin enhancer-promoter combination, but lacks a eukaryotic origin of replication. [H. Niwa, K. Yamamura, J. Miyazaki, Gene 108, 193 (1991); G. Zhang, G. Vanessa, S. R. Kain, *Biochem. Biophys. Res. Commun.* 227, 707 (1996); T. Takada et al., *Nature Biotechnol.* 15, 458 (1997)]. The 3.5 kb fragment containing the EGFP gene was obtained by digestion of the plasmid pCX-EGFP with the restriction enzymes Sal GI and Bam HI, and purified by methods known to those skilled in the art.

Purified lacZ-harboring linearized fragments of px-CANLacZ were obtained by digestion either with Sal GI or Xho I and Sal GI. The px-CANLacZ Xho I-Sal GI fragment lacks a replication origin. The β-galactosidase encoded by px-CANLacZ contains a nuclear localization signal.

In some experiments described below, a fragment of plasmid pCX-LacZ was obtained by digestion with Sal GI and Pst I to produce a pCX-LacZ Sal GI-Pst I fragment. pCX-LacZ is a derivative of pCX-EGFP in which the EGFP gene is replaced by one that encodes β-galactosidase.

Example 7

Preparation of Mixtures of DNA Fragments and Spermatozoa

Spermatozoa prepared as described above, either fresh or after they had been subjected to one of three membrane-disruption protocols: freeze-thawing, freeze-drying, or Triton X-100 extraction, were mixed with a DNA fragment, as described below.

A volume of 1 μl of the above described fragments containing the GFP gene was mixed with 9 μl of the previously prepared sperm suspensions (containing 2 to $5 \times 10^5$ spermatozoa) by pipetting to give a final DNA GFP fragment concentration of 7 ng/μl. Similarly, a volume of 1 μl of the Sal GI or Xho I/Sal GI fragments were each separately mixed with a 9 μl aliquot of the sperm suspension, to give a final Sal GI px-CANLacZ fragment concentration of 4.5 ng/μl and 9 ng/μl, respectively.

In some experiments in which single-shot double transgenesis was used to generate embryos coexpressing two tg's after a single micro-coinjection, sperm heads were mixed, prior to injection, with two transgenes, i.e., a single DNA solution containing pCX-EGFP Sal Gi-Bam HI fragment (final concentration 2.5 ng/μl) and pCX-LacZ Sal GI-Pst I fragment (final concentration 2.5 ng/μl).

The above described DNA-sperm mixtures were incubated at room temperature (about 25° C.) or on ice for 1 minute, and then mixed with a polyvinylpyrrolidone (PVP, average molecular weight 360,000) solution to give a final concentration of about 10% (w/v) PVP.

In some experiments, to determine the effect of washing the sperm after incubation with the plasmid fragment, the DNA-sperm mixtures were divided into two 5-μl aliquots immediately after mixing and incubating with pCX-EGFP DNA for 1 minute. One aliquot (washed sperm) was diluted and washed by mixing well with 50 μl of ice-cold, fresh CZB or NIM. Both aliquots were then pelleted for 2 min at 20,000×g at 2° C. The supernatant from the washed sperm aliquot was carefully removed and replaced with 5 μl of fresh CZB or NIM. The supernatant from the second aliquot was used to resuspend its own pellet. (Therefore, this sample was not washed).

In some experiments, to determine the effect of injection of the DNA fragment alone, without the coinjection of spermatozoa, a fresh dilution of the Sal GI-Bam HI fragment of plasmid pCX-EGFP (7 ng/μl in NIM) was mixed with an equal volume of PVP 20% (v/v) prior to injection.

For all experiments, the above-obtained mixtures were then placed on a microscope stage for microinjection, as described below. All injections were done in Hepes-CZB medium at room temperature within one hour of sperm-DNA mixing or within one hour of sperm-Triton X-100 mixing.

Example 8

Microinjection of Sperm Nuclei into Oocytes

For coinjection of sperm heads and exogenous DNA into the prepared oocytes, a microinjection chamber was prepared by employing the cover (10 mm in depth) of a plastic dish (100 mm×15 mm; Falcon Plastics, Oxnard, Calif., Catalogue No. 1001). A row consisting of two round droplets and one elongated droplet was placed along the center line of the dish. The first droplet (2 μl; 2 mm in diameter) was for pipette washing (Hepes-CZB containing 12% [w/v] PVP, average molecular weight 360,000 daltons). The second droplet (2 μl; 2 mm in diameter) was the mixture of spermatozoa and DNA fragment, prepared as above. The third elongated droplet (6 μl; 2 mm wide and 6 mm long) was Hepes-CZB medium for the oocytes. Each of these droplets was covered with mineral oil (E. R. Squibb and Sons, Princeton, N.J.). The dish was placed on the stage of an inverted microscope interference contrast optics.

Micro-coinjection of sperm nuclei and exogenous DNA into oocytes was achieved by the piezo-electric microinjector method described previously, employing the Piezo Micromanipulator Model MB-U by Prime Tech Ltd. (Tsukuba, Ibaraki-ken, Japan). This unit uses the piezo electric effect to advance the pipette holder a very short distance (e.g., 0.5 μm) at a time at a very high speed. The intensity and speed of the pulse were regulated by the controller.

For injection into an oocyte prepared as above, a single sperm head in mixture with the exogenous DNA was aspirated into an injection pipette (about 5 μM I.D. at the tip) which had been attached to the Piezo electric pipette driving unit. When whole spermatozoa were used, a single spermatozoa was aspirated tail first into the injection pipette. The sperm head and tail were separated by applying a single or a few Piezo pulses to the neck region. The intensity and speed (frequency) of the pulses were regulated by the controller PMAS-CT01 (controller setting scales: intensity 2, speed 1). The heads were then drawn deeply into the pipette and a small volume (about 0.5 μl) of mercury was placed in the proximal end of the injection pipette. Dislocation of the sperm heads from tails disrupts the membranes and, thus, represents a difference between the fresh spermatozoa used in these examples and previous reports of live spermatozoa promoting transgenesis by IVF.

Meanwhile, a mature unfertilized oocyte was positioned on a microscope stage in Hepes-CZB medium. The oocyte was held by a holding pipette and the tip of the injection pipette was brought into intimate contact with the zona pellucida at the 3 o'clock position. Several piezo-pulses (intensity 1–2, speed 1–2) were given to advance the pipette while a light negative pressure was applied to it. When the tip of the pipette had passed through the zona pellucida, a cylindrical piece of the zona pellucida in the pipette was expelled into the perivitelline space. After the head of the spermatozoon was pushed forward until it was near the tip of the injection pipette, the pipette was advanced mechanically until its tip almost reached the opposite side of the oocyte's cortex. The oolemma was punctured by applying 1 or 2 Piezo pulses (intensity 1–2, speed 1) and the head of the spermatozoon was expelled into the ooplasm It is estimated that about 1 picoliter (pl) of the mixture including the exogenous DNA was displaced from the pipette interior per injection. The pipette was then gently withdrawn, leaving the head of the spermatozoon within the ooplasm.

All injections were performed in Hepes-CZB at room temperature. Each oocyte was injected with one sperm head.

Approximately 5 to 20 oocytes were microinjected by this method within 10–15 minutes. Oocytes that lysed soon after injection were discarded.

In experiments to determine the effect of injection of the DNA fragment alone, without the coinjection of spermatozoa, about 1 pl of the Sal GI-Bam HI fragment of plasmid pCX-EGFP in PVP, described above, was injected per oocyte. After a recovery time of 5 to 10 min at room temperature, the injected oocytes were transferred to $Ca^{2-}$ free CZB containing 10 mM $SrCl_2$ and the cytokinesis-blocking agent cytochalasin B at 5 µg/ml, and incubated for 6 hours at 37° C. Oocytes that are not activated by spermatozoa or sperm heads must be activated by other means in order for embryonic development to take place. Activation by strontium ions is one of many parthenogenetic activation methods, known to those skilled in the art, and detailed in our copending U.S. patent application, Ser. No. 09/132,104, filed Aug. 10, 1998, the disclosure of which pertaining to oocyte activation is hereby incorporated by reference. The use of cytokinesis-blocking agents is well known to those skilled in the art, for preventing extrusion of the chromosomes. The disclosure of U.S. patent application, Ser. No.09/132,104 relating to blocking of cytokinesis in oocytes is also hereby incorporated by reference.

The parthenogenetically activated oocytes were then transferred to CZB medium and incubation continued under standard embryo culture conditions, described below. GFP expression by the embryos was scored after 3.5 days in culture, by the method described below.

Example 9

Oocyte Examination, Embryo Culture and Transfer to Surrogate Mothers

Sperm head- exogenous DNA-injected oocytes were incubated in CZB at 37° C. under mineral oil equilibrated in 5% (v/v) $CO_2$ in air and examined with an inverted microscope 5–6 hours later. Those with two distinct pronuclei and a second polar body were considered normally fertilized and cultured for 4 days in CZB. Those reaching the morula or blastocyst stages were transferred into the uterine horns of recipient females (typically CD-1 albino females) which had been mated with vasectomized (CD-1) males three days previously to synchronize embryonic developmental stages with that of the uterine endometrium. A mean number of eight morulae/blastocysts were transferred into each horn. Females were allowed to deliver and raise their surrogate offspring. Some mature male and female offspring were randomly selected and mated to examine their fertility.

Example 10

Examination of Embryos for the Expression of a Transgene

Three to 3.5 days after micro-coinjection, embryos were examined for expression of GFP by epifluorescence microscopy with a UV light source (480 nm) with fluorescein isothiocyanate filters. This enabled the clear identification of nonfluorescent (non-GFP-expressing), weakly fluorescent, and strongly fluorescent embryos and mosaics, which were scored accordingly.

Expression of the px-CANLacZ β-galactosidase was assessed in day 3 embryos, as described in T. Tsukul, et al., *Nature Biotechnology* 14, 982 (1996), after a 5-minute fixation at room temperature in phosphate-buffered saline (PBS) (pH 7.6) containing 1% (v/v) formaldehyde, 0.2% (v/v) glutaraldehyde, and BSA (5 mg/ml). Fixed embryos were washed thoroughly in PBS containing BSA (5 mg/ml) and stained by incubation for 5 hours at 37° C. in PBS containing BSA (5 mg/ml), 4 mM potassium ferricyanide, 4 mM potassium ferrocyanide, 2 mM $MgCl_2$, and 5-bromo-4-chloro-3-indolyl β-D-galactopyranoside (X-gal) (1 mg/ml). Embryos were examined and scored by light microscopy.

In experiments in which two transgenes were coinjected with the sperm heads, day 3 to 3.5 embryos were first scored for GFP expression and then for β-galactosidase expression, by the methods described above. For photograph, embryos were mounted between a microscope slide and a coverslip and images were collected to show development and GFP expression before fixation and staining to show LacZ expression.

Example 11

Examination of Live Offspring for Transgene Expression

Live offspring obtained from embryos implanted in surrogate mothers, as described above, were examined one to 4 days after delivery for expression of ectopic GFP. GFP expression was clearly observable as a green skin color under incidental illumination from a UV light source (480 nm).

Example 12

Analysis of Genomic Integration of Transgene

Physical analysis of tail-tip genomic DNA by Southern blotting or by polymerase chain reaction (PCR) was performed. Tail-tip biopsies were performed on 3- to 6-week-old, randomly selected green mouse pups and their non-green littermates. The tail-tip tissue was used for extraction of total, genomic DNA by methods well known to those skilled in the art. Photography of the tails was under a fluorescent stereomicroscope equipped with a 480/440-nm filter.

For Southern blot analysis, 10 µg of genomic DNA per sample was digested with Eco RI and probed with the 733-base-pair Eco RI fragment of pCX-EGFP. For detection of the GFP gene, PCR was performed with 1 µg of genomic DNA per reaction, using forward (TTGAATTCGCCACCATGGTGAGC) and reverse (TTGAATTCTTACTTGTACAGCTCGTCC) oligonucleotide primers. Reaction parameters were 95° C. for 9 min (1 cycle) and 94° C. for 45 seconds, 60° C. for 30 seconds, 72° C. for 45 seconds (40 cycles). PCR products were separated by electrophoresis and visualized after staining with ethidium bromide.

Figure 2A:
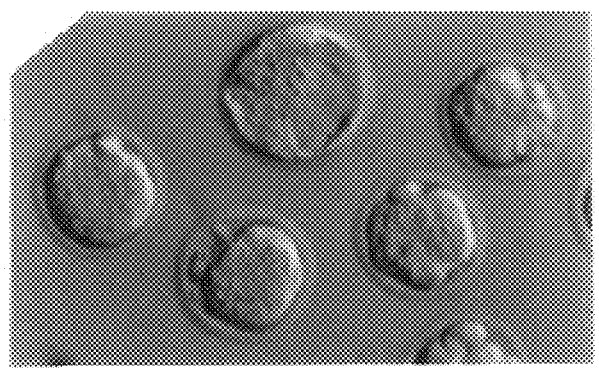
FIG. 2(A–C) is a photomicrograph illustrating transgenic embryos produced by single-shot double transgenesis. Oocytes were microinjected with spermatozoa that had been preincubated with a mixtures of pCX-LacZ and pCX-EGFP tg DNAs. The same embryos are shown (X400) after 3.5 days viewed by Hoffman modulation contrast microscopy unstained (FIG. 2A), for GFP expression under long-wavelength (480 nm) ultraviolet (UV) light (FIG. 2B), and stained with X-gal for β-galactosidase expression (FIG. 2C).
Figure 2B:
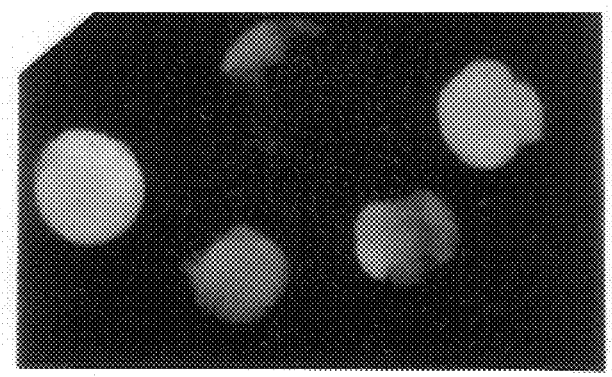
Figure 2C:
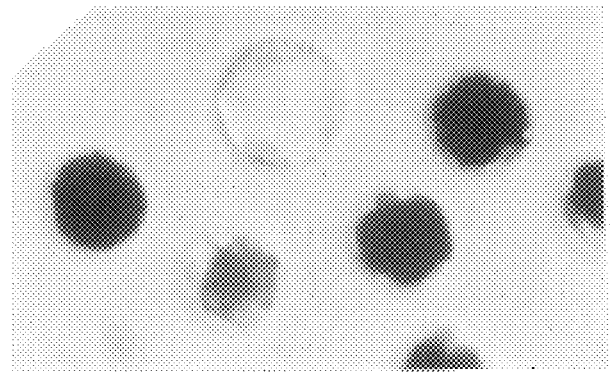

Expression of Transgene in Embryos Produced After Microinjection of Metaphase II Oocytes with Exogenous Reporter-Encoding DNA or Sperm Heads or Both Expression of GFP and β-galactosidase was recorded in embryos that had been cultured in vitro for 3.5 days after sperm and DNA were preincubated for one minute and then coinjected. GFP was detected by epifluorescence microscopy and β-galactosidase was detected by staining, as described above. The results are illustrated in Table 1. The proportion of embryos containing fluorescing blastomeres was lowest (26%) when pCX-EGFP DNA was coinjected with fresh spermatozoa, but it increased to higher values when the DNA was coinjected with spermatozoa that had been subjected to membrane disruption by Triton X-100 (64%), freeze-thawing (82%), or freeze-drying (87%). Coinjection of unfertilized oocytes with linearized px-CANLacZ DNA fragments and either freeze-thawed or freeze-dried sperm also generated a high proportion (92% to 94%) of embryos expressing the lacZ tg product β-galactosidase. Furthermore, coinjection of a sperm head with a mixture of two different tg DNAs (respectively encoding GFP and LacZ) produced embryos expressing both tg's from a single microinjection. FIG. 2 illustrates transgenic embryos produced by such a single-shot double transgenesis. Oocytes were microinjected with spermatozoa that had been preincubated with a mixture of pCX-LacZ and pCX-EGFP tg DNAs. The same embryos are shown (X400) after 3.5 days viewed by Hoffman modulation contrast microscopy unstained (FIG. 2A), for GFP expression under long-wavelength (480 nm) UV light (FIG. 2B), and stained with X-gal for β-galactosidase expression (FIG. 2C).

Collectively, the foregoing data indicate that coinjection of membrane-disrupted sperm heads and exogenous nucleic acid into unfertilized oocytes can efficiently produce transgenic embryos.

Spermatozoa that had been washed with fresh medium after being mixed with pCS-EGFP DNA retained the ability to produce fluorescent blastocysts, albeit with a slightly reduced efficiency (63% versus 80%), compared with their nonwashed counterparts (Table 1). This suggests a rapid association between exogenous DNA and spermatozoa during mixing (before injection).

To probe whether a similar interaction could occur inside the oocyte (after injection), we injected sperm heads and pCX-EGFP DNA serially, with no mixing before injection. We consistently failed to observe exogenous (GFP) DNA expression, even though 75% positive control embryos (freeze-thaw sperm head-pCX-EGFP coinjection as for Table 1) were fluorescent. Freeze-thawed sperm heads coinjected with pCX-EGFP at 500 pg/μl (but not at 50 pg/μl) produced blastocysts expressing observable GFP. This threshold of GFP detection (corresponding to 50 to 500 pg of pCX-EGFP DNA per microliter) represents an average of 15 to 150 molecules per picoliter injected.

In contrast to coinjection with a sperm head, injection of a similar quantity of GFP tg DNA alone did not preclude good parthenogenetic development (98% of oocytes surviving injection developed to the morula-blastocyst stage) (Table 1). Moreover, none of the resulting embryos exhibited observable tg expression. Hence, in the absence of sperm heads there could have been little tg expression or epichromosomal persistence of transcriptionally active tg DNA.

The data of Table 1 favor the notion of a preinjection association between exogenous DNA and sperm head submembrane structures, conceivably involving predominantly basic proteins of the perinuclear matrix [F. J. Longo et al., *J. Cell Biol.* 105, 1105 (1987)]. In other experiments in our laboratory, we have found that sperm nuclei contain at least one endonuclease and at 25° C. demembranated spermatozoa quickly lose their ability to support full embryonic development [B. Maione et al., *DNA Cell Biol.* 16, 1087 (1997). Therefore, it is unlikely that the sperm genomic DNA used here was damage-free, consistent with the presence of single-strand breaks that would facilitate oocyte-mediated tg integration.

Curiously, we observed mosaic embryos containing both GFP-positive and -negative blastomeres (+/−morulae-blastocysts) after sperm head-pCX-EGFP coinjection, but not after injection of pCX-EGFP DNA alone (Table 1). The frequency of such +/−mosaics implies that tg DNA integration was sometimes delayed until after the first S-phase of the cell cycle after ICSI. Such delayed integration apparently did not occur unless tg DNA had been coinjected with a sperm head. One interpretation of this is that sperm-derived material stabilizes exogenous DNA within the early embryo, thereby facilitating delayed integration; in the absence of such material (for example, in parthenotes) the exogenous DNA would be degraded before it could integrate.

After sperm head-pCX-EGFP coinjection, the developmental potential of embryos decreased as the proportion that contained fluorescent blastomeres increased (Table 1). In contrast, tg expression after sperm head-pxCANLacZ coinjection did not inhibit embryonic development (Table 1). Without being limited by theory, it is possible that this reflects a deleterious effect of GFP expression. That is, early embryonic development may be exquisitely sensitive to the evolution of $H_2O_2$ that accompanies maturation of the GFP chromophore (R. Y. Tsien, supra).

Figure 3A:
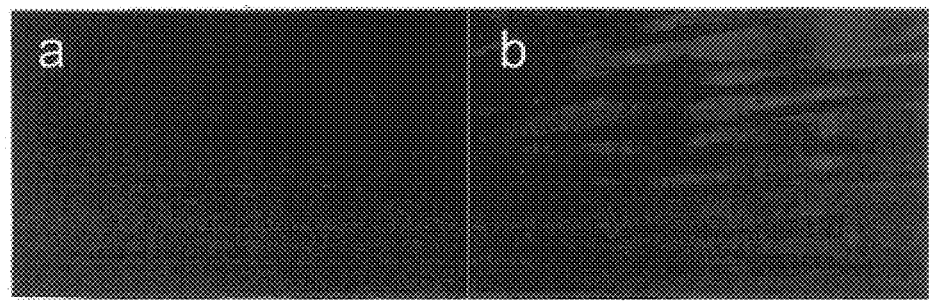
(FIG. 3A) Fluorescent stereomicroscopy (X40) of tail tips from nontransgenic (a) (mouse 16) and transgenic, green-fluorescent (b) (mouse 3) lines. Green fluorescent skin could be visualized through non-green hairs.

Expression of Transgene in Live Offspring Produced After Microinjection of Metaphase II Oocytes with Exogenous Reporter-Encoding DNA or Sperm Heads or Both To determine whether genomic integration of tg DNA constructs could be demonstrated in the live offspring (founder mice), sperm heads that had been subjected to one of the three membrane disruption procedures were coinjected with pCX-EGFP DNA. The resulting embryos were cultured in vitro, as described above, for 3.5 to 4 days (to the morula-blastocyst stage), and then transferred to surrogate mothers, nonselectively, i.e., not on the basis of fluorescence. Phenotypic analysis of tg integration was by examination of tail-tip biopsies from transgenic mice and non-transgenic control mice, illustrated in FIG. 3A(*a*) and FIG. 3A(*b*), respectively, under long-wave UV light. The green-fluorescent skin of the transgenic mice could be visualized through non-green hairs. A high proportion (17% to 21%) of offspring were transgenic with respect to observable GFP expression in the skin (Table 2). This efficiency of expression did not depend on the membrane disruption method used to prepare spermatozoa. Rates of zygotic development to term were comparable for each of the three groups of membrane-disrupted sperm heads (12% to 14%), but relatively low compared with rates obtained after microinjection of similarly treated heads in the absence of exogenous DNA.

These data are consistent with the results illustrated in Table 1. The data indicate that embryos that contain GFP-negative cells are more likely to develop to term than those with cells that are all positive. Additionally, some live offspring that scored negative are likely to have arisen from mosaic embryos that contained both GFP-positive and -negative cells at day 3.5 of culture. Without being bound by theory, it is believed that coinjected pCX-EGFP DNA may have a deleterious effect on both pre- and postimplantation embryonic development. However, it is not known whether the inhibition of postimplantation development is a consequence of tg expression or of the presence of exogenous DNA per se.

Figure 3B:
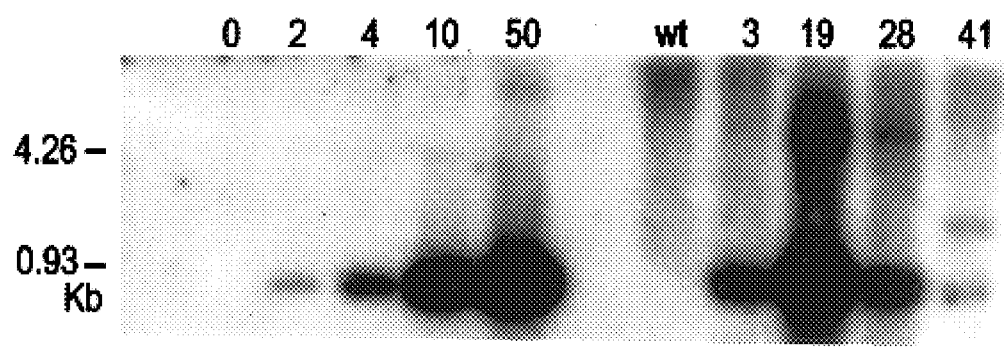
(FIG. 3B) Southern blot analysis of total DNA from control B6D2F1, (wild type, wt) (0) and from mouse number 3 (5 to 9), 19 (>50), 28 (5 to 9), and 41 (2) using a pCX-EGFP fragment as probe. Estimated tg copy numbers per genome are shown in parentheses.

Physical analysis of tail-tip total genomic DNA by Southern blotting (FIG. 3B) or by PCR (FIG. 3C) showed that all founder mouse lines that exhibited green fluorescence possessed the tg, including one that was initially scored phenotypically negative, but whose biopsied tail tip exhibited GFP expression. In three cases, the tg was demonstrated by PCR in founders that lacked detectable green fluorescence.

A random selection of 12 GFP-expressing founders (8 females, 4 males, from Table 2 and analogous series) were crossed with nontransgenic animals and produced litters in all but one case (female). Of the 11 fertile founders, 8 produced pups expressing GFP ectopically in their skin, with a frequency of 27% to 50% (average - 40%). The pattern o tg inheritance in most cases was consistent with Mendelian germ line transmission of a single locus GFP gene.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

TABLE 1

In vitro Culture and tg Expression of Embryos Produced After Microinjection of Metaphase II Oocytes With Exogenous Reporter-Encoding DNA or Sperm Heads or Both

| | | | Total morulae-blastocysts (m-b) and fluorescence (GFP) or staining (LacZ) on day 3 | | | |
|---|---|---|---|---|---|---|
| Fragment* | Sperm Treatment | No. of oocytes | m-b (%)† | −§ | +/−§ | +**§ |
| pCX-EGFP | None (fresh) | 162 | 134 (83)$^a$ | 100 | 13 | 21$^a$ |
| pCX-EGFP | Triton X-100 | 270 | 212 (79)$^a$ | 75 | 37 | 100$^b$ |
| pCX-EGFP | Freeze-thaw | 313 | 155 (50)$^b$ | 28 | 31 | 96$^b$ |
| pCX-EGFP | Freeze-dry | 278 | 154 (55)$^b$ | 20 | 23 | 111$^b$ |
| px-CANLacZ | Freeze-thaw | 151 | 110 (73)$^a$ | 7 | 45 | 58$^b$ |
| px-CANLacZ | Freeze-dry | 136 | 106 (78)$^a$ | 8 | 32 | 66$^b$ |
| pCX-EGFP | Washed | 153 | 114 (75)$^c$ | 43 | 4 | 67$^c$ |
| pCX-EGFP | Not washed | 117 | 83 (71)$^c$ | 17 | 3 | 63$^c$ |
| → ② pCX-EGFP ① pCX-EGFP → | ①Freeze-thaw | 71 | 56 (79) | 56 | 0 | 0 |
| | ②Freeze-thaw | 51 | 35 (69) | 35 | 0 | 0 |
| pCX-EGFP alone | — | 49 | 48 (98) | 48 | 0 | 0 |

*Exogenous DNA fragments were pCX-EGFP-Bam HI-Sal GI or px-CANLacZ-Sal GI, Sal G1-Xho I, or Xho I.
†When values in the same column with superscripts "a" and "b" are compared, they differ significantly (P < 0.05). Values in the same column with superscript "c" do not differ significantly.
§Tg expression: −, negative; +, positive; +/−, m-b containing both + and − cells (mosaics).

Without being bound by theory, it is believed that the nonexpression of the tg is due to locally cis-active elements at the tg integration locus. Southern blot analysis of total DNA from control B6D2F, (wt) (0) and from founder mice numbers 3 (5 to 9), 19 (>50), 28 (5 to 9), and 41 (2), using a pCX-EGFP fragment illustrated in FIG. 3B, where estimated tg copy numbers per genome are shown in parentheses. The Southern blot analysis indicated that tg copy numbers in founders ranged from ≦1 to >50. This result resembles the pattern of tg integration after pronuclear microinjection. Both the physical characterization of genomic pCX-EGFP DNA and the efficiency of GFP expression suggest that tg DNA did not undergo gross rearrangements on integration.

Figure 3C:
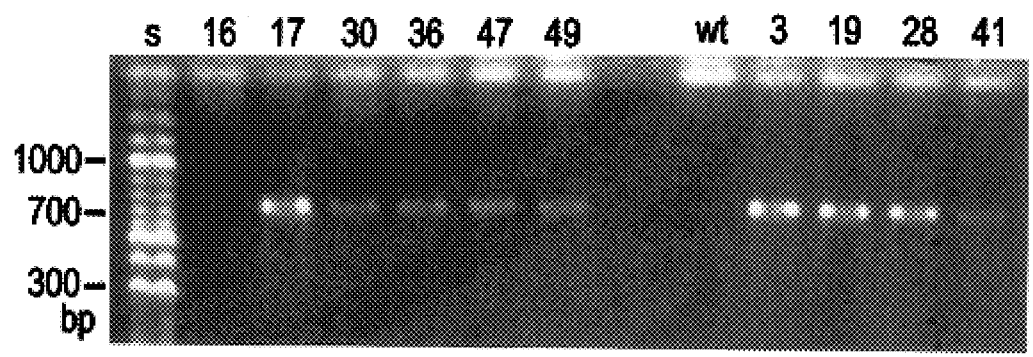
(FIG. 3C) PCR analysis of total DNA from mouse number 16, 17, 30, 36, 47, 49, control B6D2F1 (wt), mouse number 3, 19, 28, and 41.

PCR analysis of total DNA from mice 16, 17, 30, 36, 47, 49, control B6D2F1 (wt), 3, 19, 28 and 41 is illustrated in FIG. 3C and confirms the presence of the GFP transgene in mice 17, 3, 19 and 28.

TABLE 2

Development of Phenotypically Transgenic (Green) Pups and Their Siblings

| Sperm Treatment* | No. of Oocytes | m-b Transferred† | Total Pups | +(green) Pups§ |
|---|---|---|---|---|
| Freeze-dry | 116 | 67 (4) | 14 | 3** |
| Freeze-thaw | 97 | 53 (3) | 12 | 2** |
| Triton X-100 | 218 | 150 (9) | 31 | 6** |

*Each row records development of embryos and pups produced from oocytes coinjected with demembranated sperm heads and a fragment of plasmid pCX-EGFP.
†m-b, Morulae-blastocysts. Values in parentheses show the number of surrogate mothers used as recipients in embryo transfers.
§Tg expression: +, positive pups are those expressing GFP ectopically in their skin.
**Values do not differ significantly.

I claim:

1. A method for obtaining a transgenic embryo, comprising the steps of:
   incubating a nucleic acid that is exogenous to the embryo with a membrane-disrupted sperm head or a demembranated sperm head for a period of time;
   co-inserting the exogenous nucleic acid and sperm head into an unfertilized oocyte to form a transgenic fertilized oocyte; and
   allowing the transgenic fertilized oocyte to develop into a transgenic embryo.

2. The method of claim 1, wherein the co-inserting step is accomplished by piezo-electrically actuated microinjection.

3. The method of claim 2, wherein the exogenous nucleic acid and the membrane-disrupted sperm head are co-inserted into the cytoplasm of the unfertilized oocyte.

4. The method of claim 1, wherein the membrane-disrupted sperm head is obtained from a spermatozoon that has been frozen and thawed.

5. The method of claim 1, wherein the membrane-disrupted sperm head is obtained from a rehydrated freeze-dried spermatozoon.

6. The method of claim 1, wherein the sperm head is a demembranated head comprising the nucleus and perinuclear materials.

7. The method of claim 6, wherein the membrane-disrupted sperm head is obtained from a detergent-treated spermatozoon.

8. The method of claim 1, wherein the unfertilized oocyte is a metaphase II oocyte.

9. The method of claim 1, wherein the incubating time period is about 30 seconds to about 5 minutes.

10. The method of claim 9, wherein the incubating time period is about 45 seconds to about 3 minutes.

11. The method of claim 10, wherein the incubating time period is about 1 minute to about 2 minutes.

12. The method of claim 1, wherein the exogenous nucleic acid comprises more than one transgene.

13. The method of claim 1, further comprising the step of allowing the transgenic embryo to develop into a live offspring.

14. The method of claim 13, wherein the allowing step comprises the substep of transplanting the transgenic embryo into a surrogate mother.

15. The method of claim 14, wherein the mammal is selected from the group consisting of primates, ovines, bovines, porcines, ursines, felines, canines, equines and rodents.

16. The method of claim 1, wherein the oocyte and the sperm head are from a mammal.

17. The method of claim 1, wherein the oocyte and the sperm head are from an invertebrate.

18. The method of claim 1, wherein the oocyte and the sperm head are from a fish, an amphibian, a reptile or a bird.

19. The method of claim 1, wherein the oocyte and the sperm head are from a sea urchin, a lobster, an abalone, or a shellfish.

20. A method for obtaining a transgenic embryo, comprising the steps of:

obtaining a membrane-disrupted sperm head or a demembranated sperm head;

mixing the membrane-disrupted sperm head or demembranated sperm head with a nucleic acid that is exogenous to the embryo;

co-inserting the mixture into an isolated unfertilized metaphase II oocyte to form a transgenic fertilized oocyte; and allowing the transgenic fertilized oocyte to develop into a transgenic embryo.

\* \* \* \* \*

(12) EX PARTE REEXAMINATION CERTIFICATE (5818th)
United States Patent
Yanagimachi

(10) Number: US 6,376,743 C1
(45) Certificate Issued: Jul. 17, 2007

(54) MAMMALIAN TRANSGENESIS BY INTRACYTOPLASMIC SPERM INJECTION

(75) Inventor: Ryuzo Yanagimachi, Honolulu, HI (US)

(73) Assignee: University of Hawaii, Honolulu, HI (US)

Reexamination Request:
No. 90/007,737, Sep. 21, 2005

Reexamination Certificate for:
Patent No.: 6,376,743
Issued: Apr. 23, 2002
Appl. No.: 09/371,648
Filed: Aug. 10, 1999

Related U.S. Application Data

(60) Provisional application No. 60/133,970, filed on May 13, 1999, and provisional application No. 60/096,078, filed on Aug. 11, 1998.

(51) Int. Cl.
*A01K 67/033* (2006.01)
*A01K 67/00* (2006.01)
*C12N 15/87* (2006.01)
*C12N 15/89* (2006.01)

(52) U.S. Cl. .................. 800/18; 800/3; 800/13; 800/14; 800/21; 435/325; 435/455

(58) Field of Classification Search .............. None
See application file for complete search history.

(56) References Cited

PUBLICATIONS

Mohar et al. (2002) Molecular Reproduction and Development 62:416–420.*

Kroll, K.L and Amaya, E., 1996, Transgenic Xenopus embryos from sperm nuclear transplantations reveal FGF signaling requirements during gastrulation, Development, vol. 122, pp. 3173–3183.

Weltzien, H.U et al., 1979, Detergent properties of water–soluble choline phosphatides, Jour Biol Chem, vol. 254, pp. 3652–3657.

Murray, A.W., 1991, Cell Cycle Extracts, Metyhods in Cell Biology, vol. 36, pp. 581–605.

Kimura, Y. and Yanagimachi, R. 1995, Intracytoplasmic spem injection in the mouse, Biology of Reproduction, vol. 52, pp. 709–720.

Kuretake, S. et al., 1996, Fertilization and development of mouse oocytes injected with isolated sperm heads, Biology of Reproduction, vol. 55, pp. 789–795.

Songsasen, N, 1997, Birth of live mice resulting from oocyted fertilized in vitro with cryo preserved spermatozoa, Biology of Reproduction, vol. 56, pp. 143–152.

Wakayama, T. 1998, Development of normal mice from oocyted injected with freeze–dried spermatozoa, Nature Biotechnology, vol. 16, pp. 639–641.

* cited by examiner

*Primary Examiner*—Bennett M. Celsa

(57) ABSTRACT

Coinjection of unfertilized mouse oocytes with sperm heads and exogenous nucleic acid encoding a transgene results in transgene-expressing embryos, reflecting nucleic acid-sperm head association before coinjection. Nonselective transfer to surrogate mothers of embryos resulting from coinjection produced offspring expressing the integrated transgene.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 16–19 are cancelled.

Claims 1 and 20 are determined to be patentable as amended.

Claims 2–15, dependent on an amended claim, are determined to be patentable.

New claims 21 and 22 are added and determined to be patentable.

1. A method for obtaining a transgenic *mammalian* embryo, comprising the steps of:

incubating a nucleic acid that is exogenous to the embryo with a *mammalian* membrane-disrupted sperm head or a *mammalian* demembranated sperm head for a period of time;

co-inserting the exogenous nucleic acid and sperm head into an unfertilized *mammalian* oocyte to form a transgenic fertilized oocyte; and allowing the transgenic fertilized oocyte to develop into a transgenic *mammalian* embryo.

20. A method for obtaining a transgenic *mammalian* embryo, comprising the steps of:

obtaining a *mammalian* membrane-disrupted sperm head or a *mammalian* demembranated sperm head;

mixing the membrane-disrupted sperm head or demembranated sperm head with a nucleic acid that is exogenous to the embryo;

co-inserting the mixture into an isolated unfertilized *mammalian* metaphase II oocyte to form a transgenic fertilized oocyte; and allowing the transgenic fertilized oocyte to develop into a transgenic *mammalian* embryo.

21. *The method of claim 1, wherein the incubating step is performed in the absence of restriction enzymes.*

22. *The method of claim 20, wherein the incubating step is performed in the absence of restriction enzymes.*

* * * * *